United States Patent [19]

Sikorski et al.

[11] Patent Number: 4,594,093
[45] Date of Patent: Jun. 10, 1986

[54] TRIESTER DERIVATIVES OF N-PHOSPHONOMETHYLTHIONOGLYCINE AS HERBICIDES

[75] Inventors: James A. Sikorski, Kirkwood; David E. Schafer, St. Louis, both of Mo.

[73] Assignee: Monsanto Co., St. Louis, Mo.

[21] Appl. No.: 674,634

[22] Filed: Nov. 26, 1984

[51] Int. Cl.$^4$ .................. A01N 57/10; C07C 153/023
[52] U.S. Cl. .......................................... 71/87; 558/169
[58] Field of Search .................. 260/455 P; 71/87

[56] References Cited

U.S. PATENT DOCUMENTS

| 3,799,758 | 3/1974 | Franz | 260/455 R |
| 3,830,829 | 8/1974 | Olin | 260/455 R |
| 4,120,689 | 10/1978 | Dutra | 260/455 P |

OTHER PUBLICATIONS

Reid, et al., Liebigs Ann. Chem., 642, pp. 128-133 (1960).
Lowe, et al., Biochem. J., 96, pp. 189-193 (1965).
Carey, et al., Biochemistry, 21, 3102-8, (1982).
Raap, Canad. J. Chem., 46, pp. 2255-2261 (1968).
Kaloustian, et al., J. Org. Chem., 44, 666-8, (1979).
Kaloustian, et al., J. Org. Chem., 46, 5052-54 (1981).
Campbell, et al., J.A.C.S., 99, 5378-82 (1977).

*Primary Examiner*—Henry R. Jiles
*Assistant Examiner*—Robert C. Whittenbaugh
*Attorney, Agent, or Firm*—David Bennett; Paul D. Matukaitis; Arnold H. Cole

[57] ABSTRACT

This invention relates to triester derivatives of N-phosphonomethylthionoglycine which represent a new class of organic chemical compounds. This invention further relates to herbicidal compositions and methods employing such compounds.

20 Claims, No Drawings

TRIESTER DERIVATIVES OF N-PHOSPHONOMETHYLTHIONOGLYCINE AS HERBICIDES

This invention relates to triester derivatives of N-phosphonomethylthionoglycine which represent a new class of organic chemical compounds. This invention further relates to herbicidal compositions containing such derivatives and to herbicidal methods employing such compounds and compositions.

BACKGROUND OF THE INVENTION

U.S. Pat. No. 3,799,758 issued to John E. Franz on Mar. 26, 1974 describes the preparation and herbicidal utility of N-phosphonomethylglycine and its esters, amides, and salts.

U.S. Pat. No. 4,120,689 issued to Gerard A. Dutra on Oct. 17, 1978 describes alkyl[di-(benzyl) or di-(aryl)] esters of N-phosphonomethylglycine which are produced by the reaction of a dibenzyl or diaryl phosphite with an N-methylene alkyl glycinate trimer. These esters and the hydrolysis products thereof containing at least one benzyloxy or aryloxy group bonded to phosphorous are compounds disclosed as having the formula

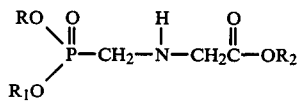

wherein

R is a member of the group consisting of phenyl, benzyl, naphthyl, biphenyl, and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro or halo;

$R_1$ is hydrogen or an R group; and $R_2$ is a lower alkyl group or hydrogen, and the strong acid salts of the compounds wherein neither $R_1$ or $R_2$ is H. These compounds are useful as postemergent herbicides.

Several N-protected thionoglycinate esters are described in the chemical literature. Specifically, the sulfonamide-protected derivative represented by the formula

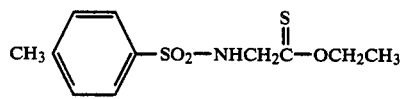

has been demonstrated by W. Reid and W. Von der Emden [Liebigs Ann. Chem., 642, 128-33 (1960)]. Carboxamide protecting groups have also been frequently employed to produce derivatives represented by the formula

Specific examples include those wherein R is phenyl and $R_1$ is methyl [G. Lowe and A. Williams, Biochem. J., 96, 189-93 (1965); wherein R is benzyloxy and $R_1$ is ethyl [W. Reid and W. Emden, ibid]; and wherein R is benzyl or phenethyl and $R_1$ is methyl [P. R. Carey et al, Biochemistry, 21, 3102-8 (1982)].

However, there are no examples in the chemical literature of fully deprotected thionoglycinate esters or simple N-alkyl derivatives thereof which are stable at room temperature and are represented by the formula

wherein $R_1$ is hydrogen or an alkyl group, and $R_2$ is lower alkyl.

It will be apparent from a study of the above patents and publications that none of them disclose or suggest thionoglycinate esters containing an N-[(diaryloxyphosphinyl)methyl]group. In fact, one would anticipate that such compounds could not be prepared in light of the known facile reaction between thiono ester groups and primary or secondary amines [R. Rapp, Canad. J. Chem., 46, 2255-61 (1968); M. K. Kaloustian et al, J. Org. Chem., 44, 666-8 (1979); M. K. Kaloustian and R. B. Nader, J. Org. Chem., 46, 5052-54, (1981)], as well as amino acids, [P. Campbell and B. A. Lapinskas, J. Am. Chem. Soc., 99, 5378-82 (1977)] at room temperature.

BRIEF SUMMARY OF THE INVENTION

In accordance with the present invention, there is provided novel triester derivative of N-phosphonomethylthionoglycine which exhibit unique chemical stability and are represented by the formula

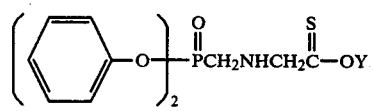

wherein Y is an alkyl group containing 2-6 carbon atoms as well as the strong acid salts of these compounds. The above described compounds are herbicidally active.

DETAILED DESCRIPTION OF THE INVENTION

The compounds of this invention are prepared by reacting an appropriate acetamidic ester described in U.S. Pat. No. 4,104,050 to Dutra of the formula

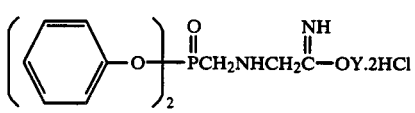

wherein Y is as aforedefined with hydrogen sulfide in the presence of a hydrogen chloride acceptor to form a compound of Formula I.

The reaction temperature for the aforerecited reaction is in the range from about $-50°$ C. to about $+100°$ C., and is preferably from about $-30°$ C. to about $+30°$ C., although greater or lower temperatures may be employed if desired.

The hydrogen chloride acceptor is typically an amine, preferably a tertiary amine, which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof, and the like.

The compounds of Formula I represent the first known recoverable examples of simple N-alkylthionoglycinate derivatives. As such, they represent a unique class of organic compounds which incorporate a reactive thiono ester moiety in the same molecule as a reactive secondary amine group.

The chemical behavior of the amine function in compounds of Formula I was characterized as typical of a secondary amine by salt formation and amide derivatization. The compounds of Formula I can be treated with a strong acid to form strong acid salts of the formula

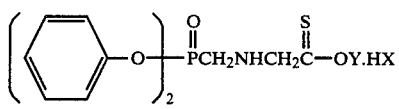

III wherein Y is as aforedefined, and HX is a strong acid. These salts are also herbicidally active.

The strong acid salts of compounds of Formula III are produced by dissolving compounds of Formula I in a suitable inert solvent, such as ethyl acetate or chloroform, and then adding a strong acid. The salt precipitates or a nonsolvent for the salt is added, such as diethyl ether, and the salt forms an insoluble oil or a solid.

The strong acids which can be employed to produce compounds of Formula III are those which have a pKa of 2.2 or less as measured in aqueous solution. Examples of suitable acids include hydrochloric, hydrobromic, hydriodic, methane sulfonic, benzene sulfonic, p-nitrobenzene sulfonic, trifluoroacetic, and the like.

The compounds of Formula I also react with trifluoroacetic anhydride in an inert aprotic solvent and in the presence of a suitable acid scavenger to produce compounds of the formula

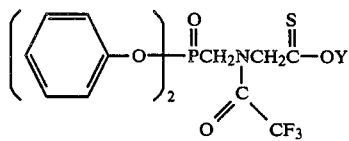

IV wherein Y is as aforedefined. These trifluoroacetamide derivatives also have limited herbicidal properties.

The chemical reactivity of the thiono ester group in the compounds of Formula I was characterized as typical of other known thiono esters by reaction with piperidine to produce a thioamide of the formula

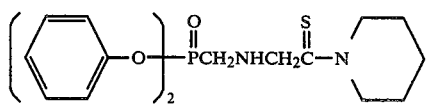

V

The term "alkyl" is employed throughout the claims and description to mean a monovalent radical in a straight, cyclic, or branched chain, usually of the formula $C_nH_{2n+1}$, wherein n is an integer from 2 to 6.

Typical groups representative of the term "alkyl" include, for example, ethyl, propyl, isopropyl, butyl, neo-pentyl, cyclohexyl, and the like.

The following illustrative, nonlimiting examples will serve to further demonstrate to those skilled in the art the process of this invention wherein specific compounds within the scope of this invention can be prepared.

EXAMPLE I

Ethanethioic Acid, 2-[[(Diphenoxyphosphinyl)Methyl]Amino]-O-Ethyl Ester

α-[[(diphenoxyphosphinyl)methyl]amino]acetamidic acid, ethyl ester dihydrochloride was prepared as a white solid from diphenyl-N-phosphonomethylglycinonitrile (9.1 g, 0.03 mole) and absolute ethanol (2.8 g, 0.06 mole). This solid was dissolved in 150 ml of dry, distilled pyridine at −10° C. Then H$_2$S was bubbled in for 2 hours. The resulting heterogeneous mixture was stirred overnight at 0° C., filtered, and concentrated in vacuo to give a yellow oil. This oil was partitioned between diethyl ether and water. The ether layer was separated, dried over MgSO$_4$, filtered, and concentrated to give a yellow oil (7.2 g, 66%). This oil slowly crystallized on standing at room temperature to give ethanethioic acid, 2-[[(diphenoxyphosphinyl)methyl]amino]-O-ethyl ester as a yellow solid, m.p. 52°–54° C., corresponding to a compound of Formula I wherein Y is ethyl. NMR($^1$H, $^{31}$P, $^{13}$C), IR, and TLC results were all consistent with pure product.

Anal. Calc'd. for C$_{17}$H$_{20}$NO$_4$PS: C, 55,88; H, 5.52; N, 3.83; S, 8.78. Found: C, 55.62; H, 5.60; N, 3.80; S, 8.67.

EXAMPLE 2

Ethanethioic Acid, 2-[[Diphenoxyphosphinyl)Methyl]Amino]-O-(2,2-Dimethylpropyl) Ester α-[[(diphenoxyphosphinyl)methyl]amino]acetamidic acid, (2,2-dimethylpropyl) ester dihydrochloride was prepared as a white solid from diphenyl-N-phosphonomethylglycinonitrile (24.2 g, 0.08 mole) and neopentyl alcohol (14.1 g, 0.16 mole). This solid was dissolved in 300 ml of dry, distilled pyridine at −10° C. Then H$_2$S was bubbled in for 3 hours. The resulting heterogeneous mixture was maintained overnight at 0° C., filtered, and concentrated in vacuo to give a yellow oil. This oil was partitioned between ether and water. The ether layer was washed with cold 10% aqueous NaOH, separated, dried over MgSO$_4$, filtered, and concentrated to give 8.0 g of an orange oil. This oil was further purified by flash chromatography on silica gel eluting with 40% cyclohexane/60% ethyl acetate to give ethanethioic acid, 2-[[(diphenoxyphosphinyl)methyl]amino]-O-(2,2-dimethylpropyl) ester as a yellow oil (4.6 g) with a refractive index n$_D^{27.5}$=1.6650 corresponding to a compound of Formula I wherein Y is neo-pentyl. NMR ($^1$H, $^{31}$P, $^{13}$C), IR, and TLC results were all consistent with pure product.

Anal. Calc'd. for C$_{20}$H$_{26}$NO$_4$PS: C, 58.95; H, 6.43; N, 3.44; S, 7.87. Found: C, 58.90; H, 6.44; N, 3.44; S, 7.77.

EXAMPLE 3

Ethanethioic Acid, 2-[[(Dipenoxyphosphinyl)Methyl]Amino]-O-(1-Methylethyl) Ester α-[[(diphenoxyphosphinyl)methyl]amino]acetamidic acid, (1-methylethyl) ester dihydrochloride was prepared as a white solid from diphenyl-N-phosphonomethylglycinonitirile (24.2 g, 0.08 mole) and isopropanol (6.2 ml, 0.08 mole). This solid was dissolved at −10° C. in 300 ml of dry, distilled pyridine. Then $H_2S$ was bubbled in for 2 hours. The resulting heterogeneous mixture was stirred at 0° C. for 1 hour, filtered, and concentrated in vacuo to give a yellow oil. This oil was partitioned between diethyl ether and water. The ether layer was separated, dried over $MgSO_4$, filtered, and concentrated to give a yellow oil (16 g, yield 53%). This oil slowly crystallized on standing in a freezer to give ethanethioic acid, 2-[[(diphenoxyphosphinyl)methyl]amino]-O-(1-methylethyl) ester as a light brown solid, m.p. 40°–43° C., corresponding to a compound of Formula I wherein Y is isopropyl. NMR ($^1H$, $^{31}P$, $^{13}C$), IR, and TLC results were all consistent with pure product.

Anal. Calc'd. for $C_{18}H_{22}NO_4PS$: C, 56.98; H, 5.84; N, 3.69; S, 8.45. Found: C, 56.83; H, 5.88; N, 3.66; S, 8.44.

EXAMPLE 4

Ethanethioic Acid, 2-[[(Diphenoxyphosphinyl)Methyl]Amino]-O-Ethyl Ester, p-Nitrobenzene Sulfonic Acid Salt 2.0 g (0.0055 mole) of ethanethioic acid, 2-[[(diphenoxyphosphinyl)methyl]amino]-O-ethyl ester was dissolved in 100 ml of acetonitrile. Then p-nitrobenzene sulfonic acid (1.1 g, 0.0055 mole) was added. When no crystallization occurred, the resulting solution was concentrated in vacuo to give a yellow oil. This oil could be successfully crystallized by dissolving it in a minimum amount of ethyl acetate and then adding diethyl ether to the cloud point. This produced ethanethioic acid, 2-[[(diphenoxyphosphinyl)methyl]amino]-O-ethyl ester, p-nitrobenzene sulfonic acid salt as white needles (2.1 g, yield 67%), m.p. 64°–66° C.

Anal. Calc'd. for $C_{23}H_{25}N_2O_9PS_2$: C, 48.59; H, 4.43; N, 4.93; S, 11.28. Found: C, 48.58; H, 4.45; N, 4.90; S, 11.25.

EXAMPLE 5

Ethanethioic Acid, 2-[[(Diphenoxyphosphinyl)Methyl]Amino]-O-(2,2-Dimethylpropyl) Ester, Methane Sulfonic Acid Salt 1.00 g (0.0024 mole) of ethanethioic acid, 2-[[(diphenoxyphosphinyl)methyl]amino]-O-(2,2-dimethylpropyl) ester was dissolved in 5 ml of deuterochloroform. Then 1 equivalent of methanesulfonic acid (0.24 g, 0.0024 mole) was added. When no crystallization occurred, the resulting solution was concentrated in vacuo to give a yellow oil. This oil crystallized upon standing under vacuum at room temperature. This produced ethanethioic acid, 2-[[(diphenoxyphosphinyl)methyl]amino]-O-(2,2-dimethylpropyl) ester, methane sulfonic acid salt as a light yellow solid, (1.0 g, yield 80%), m.p. 93°–95° C.

Anal. Calc'd. for $C_{21}H_{30}NO_7PS_2$: C, 50.09; H, 6.00; N, 2.78; S, 12.73. Found: C, 49.81; H, 5.90; N, 2.92; S, 12.86.

EXAMPLE 6

Ethanethioic Acid, 2-[[(Diphenoxyphosphinyl)Methyl](Trifluoroacetyl)Amino]-O-(2,2-Dimethylpropyl) Ester Ethanethioic acid, 2-[[(diphenoxyphosphinyl)methyl]amino]-O-(2,2-dimethylpropyl) ester (5.0 g, 0.012 mole) was dissolved in 200 ml of toluene containing triethylamine (2.5 g, 0.024 mole). Then trifluoroacetic anhydride (5.1 g, 0.024 mole) was carefully added dropwise. A vigorous reaction occurred. The resulting heterogeneous mixture was maintained at room temperature for 3 days, then cold 5% aqueous NaOH was added. The toluene layer was separated and concentrated to give 3.0 g (50%) of an orange oil. This oil was further purified by flash chromatography on silica gel eluting with 60% cyclohexane/40% ethyl acetate to give ethanethioic acid, 2-[[(diphenoxyphosphinyl)methyl(trifluoroacetyl)amino]-O-(2,2-dimethylpropyl) ester as a waxy yellow solid, m.p. 41°–44° C., corresponding to a compound of Formula IV wherein Y is neo-pentyl. NMR ($^1H$, $^{31}P$), IR, and TLC results were all consistent with pure product.

Anal. Calc'd. for $C_{22}H_{25}F_3NO_5PS$: C, 52.48; H, 5.01; S, 6.37. Found: C, 52.47; H, 5.04; S, 6.36.

EXAMPLE 7

Ethanethioic Acid, 2-[[(Diphenoxyphosphinyl)Methyl](Trifluoroacetyl)Amino]-O-(1-Methylethyl) Ester Ethanethioic acid, 2-[[(diphenoxyphosphinyl)methyl]amino]-O-(1-methylethyl) ester (5.0 g, 0.013 mole) was dissolved in 200 ml of toluene containing triethylamine (2.7 g, 0.026 mole). Then trifluoroacetic anhydride (5.50 g, 0.026 mole) was carefully added dropwise. A vigorous reaction occurred. The resulting heterogeneous reaction was maintained at room temperature for 3 days, then cold 5% aqueous NaOH was added. The toluene layer was washed with an equal volume of water, separated, dried over $MgSO_4$, filtered, and concentrated to give an orange oil (4.2 g, yield 67%), corresponding to a compound of Formula IV wherein Y is isopropyl. NMR ($^1H$, $^{31}P$), IR, and TLC results were all consistent with pure product.

Anal. Calc'd. for $C_{20}H_{21}F_3NO_5PS$: C, 50.53; H, 4.45; N, 2.95; S, 6.74. Found: C, 50.37; H, 4.51; N, 3.13; S, 7.20.

EXAMPLE 8

Ethanethioic Acid, 2-[[(Diphenoxyphophinyl)Methyl](Trifluoroacetyl)Amino]-O-Ethyl Ester Ethanethioic acid, 2-[[(diphenoxyphosphinyl)methyl]amino]-O-ethyl ester (7.3 g, 0.02 mole) was dissolved in 250 ml of toluene containing triethylamine (4.05 g, 0.04 mole). Then trifluoroacetic anhydride (8.4 g, 0.04 mole) was carefully added dropwise. A vigorous reaction occurred. The resulting heterogeneous mixture was maintained at room temperature for 3 days, then 200 ml of cold water was added. The toluene layer was washed with an equal volume of cold 5% aqueous NaOH and then water, separated, dried over $MgSO_4$, filtered, and concentrated to give 6.0 g of an orange oil which solidified upon storage in a freezer. Tritration with petroleum ether gave ethanethioic acid, 2-[[(diphenoxyphosphinyl)methyl](trifluoroacetyl)amino]-O-ethyl ester as a light yellow solid (2.80 g, yield 30%). m.p. 71°–72° C., corresponding to a compound of Formula IV wherein Y is ethyl. NMR ($^1H$, $^{31}P$), IR, and TLC results were all consistent with pure product.

Anal. Calc'd. for $C_{19}H_{19}F_3NO_5PS$: C, 49.46; H, 4.16; N, 3.04; S, 6.95. Found: C, 49.61; H, 4.21; N, 3.19; S, 7.37.

EXAMPLE 9

Phosphonic Acid,
[[[2-(1-Piperidinyl)-2-Thioxoethyl]Amino]Methyl]-,
Diphenyl Ester Ethanethioic acid, 2-[[(diphenoxyphosphinyl)methyl]amino]-O-ethyl ester (8.8 g, 0.024 mole) was dissolved under nitrogen in 200 ml of diethyl ether. Piperidine (2.05 g, 0.024 mole) was then added, and the resulting solution was stirred overnight at room temperature. The ether layer was decanted away from a dark insoluble oil. The ether layer was absorbed on to 20 g of silica gel and purified by column chromatography eluting with 20% cyclohexane/80% ethyl acetate to give phosphonic acid, [[[2-(1-piperidinyl)-2-thioxoethyl]amino]-methyl]-, diphenyl ester as a yellow oil (1.7 g, yield 20%), $n_D^{26.5} = 1.5870$. NMR ($^1H$, $^{31}P$) and TLC results were all consistent with pure product.

Anal. Calc'd. for $C_{20}H_{25}N_2O_3PS$: C, 59.39; H, 6.23; N, 6.93; S, 7.93. Found: C, 59.32; H, 6.29; N, 6.77; S, 7.76.

EXAMPLE 10

The post-emergence herbicidal activity of some of the compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for ther perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks) each pan, except for the control pans, is removed individually to a spraying chamber and sprayed by means of an atomizer operating at a positive air pressure of approximately 1.46 kg/cm$^2$ absolute. The atomizer contains 6 ml of a solution or suspension of the chemical. In that 6 ml is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The sprays solution is prepared by taking an aliquot of a 1.0% by weight stock solution or suspension of the candidate chemical in an organic solvent, such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
|---|---|
| less than 25% inhibition | 0 |
| 25 to less than 50% inhibition | 1 |
| 50 to less than 75% inhibition | 2 |
| 75 to 99% inhibition | 3 |
| 100% inhibition (complete kill) | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morning Glory | N - Wheat |
| E - Lambsquarters, Common | O - Rice |
| F - Smartweed, Pennsylvania | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass, Large |

*Established from vegetative propagules.

The letter "N" in the tables indicates that the particular species was absent in the test.

TABLE I

| Compound of Example No. | WAT | kg/h | A | B | C | D | E | F | G | H | I | J | K |
|---|---|---|---|---|---|---|---|---|---|---|---|---|---|
| I | 2 | 11.2 | 2 | 3 | 3 | 2 | 3 | 4 | 2 | 3 | 3 | 1 | 3 |
|   | 4 |      | 4 | 4 | 4 | 4 | 4 | 4 | 3 | 3 | 4 | 3 | 4 |
|   | 2 | 5.6  | 4 | 2 | 3 | 2 | 2 | 4 | 1 | 3 | 4 | 1 | 3 |
|   | 4 |      | 4 | 4 | 4 | 4 | 3 | 4 | 2 | 3 | 4 | 3 | 4 |
| II | 2 | 11.2 | 2 | 1 | 1 | 1 | 2 | 4 | 2 | 1 | 2 | 0 | 3 |
|    | 4 |      | 1 | 2 | 3 | 2 | 2 | 4 | 2 | 2 | 3 | 2 | 3 |
|    | 2 | 5.6  | 0 | 1 | 1 | 1 | 0 | 1 | 0 | 0 | 2 | 1 | 1 |
|    | 4 |      | 0 | 1 | 1 | 2 | 2 | 2 | 2 | 1 | 3 | 2 | 2 |
| III | 2 | 11.2 | 1 | 1 | 1 | 2 | 1 | 4 | 2 | 1 | 3 | 1 | 2 |
|     | 4 |      | 2 | 2 | 1 | 2 | 3 | 4 | 2 | 1 | 4 | 1 | 3 |
|     | 2 | 5.6  | 1 | 1 | 1 | 1 | 1 | 1 | 1 | 2 | 0 | 0 | 2 |
|     | 4 |      | 1 | 1 | 1 | 2 | 2 | 4 | 2 | 3 | 2 | 1 | 3 |
| IV | 2 | 11.2 | 2 | 2 | 3 | 3 | 3 | 3 | 2 | 2 | 3 | 2 | 3 |
|    | 4 |      | 4 | 3 | 4 | 4 | 4 | 4 | 3 | 4 | 3 | 3 | 4 |
|    | 2 | 5.6  | 2 | 2 | 2 | 2 | 2 | 1 | 3 | 1 | 0 | 1 | 0 | 3 |
|    | 4 |      | 4 | 3 | 3 | 3 | 3 | 4 | 2 | 2 | 3 | 3 | 4 |
| V | 2 | 11.2 | 1 | 2 | 1 | 1 | 3 | 4 | 1 | 0 | 1 | 1 | 1 |
|   | 4 |      | 1 | 4 | 2 | 2 | 3 | 4 | 2 | 1 | 3 | 2 | 3 |
|   | 2 | 5.6  | 2 | 1 | 2 | 2 | 3 | 2 | 1 | 1 | 3 | 2 | 2 |
|   | 4 |      | 2 | 1 | 1 | 2 | 3 | 2 | 2 | 1 | 3 | 2 | 3 |

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| I | 2 | 5.6 | 4 | 4 | 3 | 3 | 4 | 3 | 4 | 4 | 1 | N | 4 | 3 | 2 | 4 | 4 | 4 |
|  | 4 |  | 4 | 4 | 4 | 4 | 4 | 4 | 4 | 4 | 2 | N | 4 | 4 | 3 | 4 | 4 | 4 |
|  | 2 | 1.12 | 3 | 4 | 2 | 2 | 3 | 2 | 2 | N | 4 | N | 3 | 2 | 1 | 3 | 3 | 4 |
|  | 4 |  | 3 | 4 | 3 | 2 | 4 | 2 | 2 | N | 4 | N | 4 | 4 | 1 | 4 | 4 | 4 |
|  | 2 | .28 | 1 | 0 | 2 | 0 | 1 | 1 | 2 | 1 | 0 | 1 | 2 | 1 | 1 | 2 | 2 | 2 |
|  | 4 |  | 1 | 1 | 1 | 0 | 2 | 2 | 1 | 2 | 0 | 2 | 2 | 1 | 1 | 2 | 3 | 3 |
| II | 2 | 5.6 | 2 | 3 | 3 | 2 | 3 | N | 3 | 3 | N | 3 | 4 | 3 | 3 | 4 | 3 | 4 |
|  | 4 |  | 3 | 3 | 3 | 3 | 4 | N | 4 | 4 | N | 4 | 4 | 4 | 3 | 4 | 4 | 4 |
|  | 2 | 1.12 | 1 | 0 | 2 | 1 | 1 | 0 | 2 | 2 | 1 | 2 | 1 | 2 | 1 | 3 | 2 | 3 |
|  | 4 |  | 1 | 1 | 1 | 1 | 2 | 0 | 2 | 2 | 1 | 3 | 1 | 1 | 1 | 3 | 3 | 3 |
|  | 2 | .28 | 0 | 1 | 1 | 0 | 1 | N | 2 | 1 | 0 | 3 | 3 | 1 | 0 | 3 | 1 | 3 |
|  |  |  | 0 | 1 | 1 | 0 | 1 | N | 2 | 2 | 2 | 3 | 3 | 1 | 0 | 3 | 1 | 3 |
| III | 2 | 5.6 | 3 | 3 | 2 | 1 | 3 | 1 | 2 | 2 | 1 | 2 | 3 | 2 | 1 | 4 | 3 | 4 |
|  | 4 |  | 3 | 4 | 3 | 2 | 3 | 1 | 3 | 2 | 2 | 3 | 4 | 2 | 2 | 4 | 3 | 4 |
|  | 2 | 1.12 | 1 | 2 | 2 | 1 | 2 | 1 | 1 | 2 | 1 | 2 | 2 | 2 | 2 | 4 | 3 | 2 |
|  | 4 |  | 1 | 3 | 2 | 3 | 3 | 1 | 1 | 2 | 1 | 3 | 4 | 2 | 2 | 4 | 3 | 3 |
|  | 2 | .28 | 1 | 4 | 1 | 2 | 1 | 1 | 1 | 2 | 1 | N | 2 | 1 | 1 | 3 | 1 | 2 |
|  | 4 |  | 1 | 4 | 1 | 2 | 2 | 0 | 1 | 2 | 4 | N | 1 | 1 | 1 | 3 | 2 | 2 |
| IV | 2 | 5.6 | 3 | 4 | 4 | 3 | 3 | 3 | 3 | 4 | 3 | 3 | 4 | 3 | 3 | 4 | 4 | 4 |
|  | 4 |  | 3 | 4 | 4 | 3 | 4 | 4 | 3 | 4 | 4 | 4 | 4 | 4 | 3 | 4 | 4 | 4 |
|  | 2 | 1.12 | 2 | 3 | 3 | 3 | 3 | 2 | 2 | 3 | 1 | 4 | 4 | 2 | 3 | 4 | 3 | 4 |
|  | 4 |  | 2 | 3 | 3 | 3 | 4 | 3 | 3 | 4 | 1 | 4 | 4 | 3 | 3 | 4 | 4 | 4 |
|  | 2 | .28 | 1 | 1 | 1 | 0 | 1 | 2 | 1 | 2 | 1 | 2 | 2 | 2 | 1 | 3 | 3 | 3 |
|  | 4 |  | 1 | 1 | 2 | 0 | 3 | 2 | 1 | 2 | 1 | 1 | 1 | 1 | 1 | 4 | 3 | 3 |
|  | 2 | .056 | 0 | 0 | 0 | 0 | 1 | 0 | 1 | 2 | 0 | 0 | 1 | 0 | 1 | 2 | 2 | 2 |
|  | 4 |  | 0 | 1 | 0 | 0 | 1 | 0 | 1 | 1 | 0 | 0 | 1 | 0 | 0 | 3 | 2 | 1 |
| V | 2 | 5.6 | 2 | 2 | 2 | 1 | 2 | 2 | 2 | 2 | 2 | 4 | 3 | 2 | 1 | 3 | 2 | 3 |
|  | 4 |  | 2 | 2 | 2 | 1 | 2 | 2 | 3 | 2 | 2 | 4 | 3 | 3 | 2 | 3 | 3 | 3 |
|  | 2 | 1.12 | 1 | 1 | 2 | 0 | 1 | 2 | 2 | 2 | 2 | 2 | 2 | 2 | 1 | 1 | 2 | 3 |
|  | 4 |  | 1 | 2 | 2 | 0 | 2 | 1 | 1 | 1 | 2 | 2 | 2 | 1 | 1 | 1 | 2 | 3 |
|  | 2 | 5.6 | 1 | 1 | 2 | 1 | 2 | 3 | 2 | 2 | 1 | 4 | 4 | 2 | 2 | 3 | 3 | N |
|  | 4 |  | 1 | 3 | 2 | 3 | 4 | 3 | 2 | 2 | 1 | 4 | 4 | 3 | 3 | 3 | 3 | N |
|  | 2 | 1.12 | 1 | 1 | 1 | 0 | 1 | 0 | 1 | 1 | 1 | 1 | 1 | 0 | 2 | 3 | 2 | 3 |
|  | 4 |  | 1 | 1 | 2 | 0 | 3 | 0 | 1 | 1 | 0 | 2 | 0 | 0 | 3 | 3 | 2 | 3 |
|  | 2 | .28 | 1 | 0 | 0 | 0 | 1 | 0 | 1 | 0 | 0 | 1 | 0 | 0 | 0 | 1 | 1 | 1 |
|  | 4 |  | 1 | 0 | 1 | 0 | 1 | 0 | 0 | 0 | 0 | 1 | 0 | 0 | 0 | 1 | 0 | 1 |

From the test results presented in Tables I and II, it can be seen that the post-emergent herbicidal activity of the compounds of this invention is, for the most part, general in nature. In this regard it should be recognized that each individual species selected for the above tests is a representative member of a recognized family of plant species.

Typically, herbicidal compounds of this invention are provided in the form of concentrates which require dilution prior to application to plants. The usual means for diluting the herbicide is the preparation of herbicidal compositions wherein the compound possessing herbicidal activity is mixed with other materials. Such other materials may be in either liquid or solid form and comprise adjuvants, inert materials, etc.

The herbicidal composition containing herbicidal compounds of this invention are prepared in the usual manner by combining them with other materials which are well known in the herbicide art. The following is a description of herbicidal compositions employing the herbicidal compounds of this invention together with known materials and formulations typically utilized in the herbicide art.

The herbicidal compositions, including concentrates which require dilution prior to application to the plants, of this invention contain from 5 to 95 parts by weight of at least 1 compound of this invention and from 5 to 95 parts by weight of an adjuvant in liquid or solid form, for example, from about 0.25 to 25 parts by weight of wetting agent, from about 0.25 to 25 parts by weight of a dispersant, and, from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least 1 compound of this invention, together with the adjuvants. Where required, from about 0.1 to 2.0 parts by weight of the inert liquid extender can be replaced by a corrosion inhibitor, such as ethanol mercaptan, sodium thiosulfate, dodecylmono or dimercaptan, or antifoaming agent, such as a dimethylpolysiloxane or both. The compositions are prepared by admixing the active ingredient with an adjuvant including diluents, extenders, carriers, and conditioning agents to provide compositions in the form of finely-divided particulate solids, pellets, solutions, dispersions, or emulsions. Thus, the active ingredient can be used with an adjuvant, such as a finely-divided solid, a liquid of organic origin, water, a wetting agent, a dispersing agent, an emulsifying agent, or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents, and emulsifying agents are included therein. Anionic, cationic, and nonionic agents can be used with equal facility.

Preferred wetting agents are alkyl benzene and alkyl naphthalene sulfonates, sulfated fatty alcohols, amines or acid amides, long chain acid ester of sodium isothionate, esters of sodium sulfosuccinate, sulfated or sulfonated fatty acid esters, petroleum sulfonates, sulfonated vegetable oils, polyoxyethylene derivatives of phenols and alkylphenols (particularly isooctylphenol and nonylphenol), and polyoxyethylene derivatives of the mono-higher fatty acid esters of hexitol anhydrides (e.g., sorbitan). Preferred dispersants are methyl celluose, polyvinyl alcohol, sodium lignosulfonates, polymeric alkyl naphthalene sulfonates, sodium naphthalene sulfonate, polymethylene bisnaphthalene-sulfonate, and sodium N-methyl-N-(long chain acid)-laurates.

When operating in accordance with the present invention, effective amounts of the compounds or compositions of this invention are applied to the plants or are incorporated into aquatic media in any convenient fashion. The application of liquid and particulate solid compositions to plants or soil can be carried out by conventional methods, e.g., power dusters, boom and hand sprayers, and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors, as the plant species and stage of development thereof, and the amount of rainfall as well as the specific compound employed. In foliar treatment for the control of vegetative growth, the active ingredients are applied in amounts from about 0.112 to about 56.0 or more kilograms per hectare. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof, and the like. These forms may be assembled in any manner desired including a pipe rope wick, a wedge rope wick, a multi-rope wick, and the like.

In another possible application method, liquid compositions may be selectively applied to weeds by the use of recirculating sprayer systems wherein the recirculating spray unit is mounted on a tractor or high clearance mobile equipment, and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in "Innovative Methods of Post-Emergence Weed Control", McWhorter, C. G., Southern Weed Science Society, 33rd Annual Meeting Proceedings, Jan. 15-17, 1980; Auburn University Printing Service, Auburn, Ala., U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3-4; "The Recirculating Sprayer and Roundup ® Herbicide", Derting, Claude W., pp. 5-7; and "C.D.A. Herbicide Application", McGarvey, Frank X., *Weeds Today*, Volume 11, Number 2, pp. 8-9, Late Spring, 1980, 309 W. Clark St., Champaign, Ill., U.S.A., the teachings of which are incorporated herein by reference in their entirety.

Although this invention has been described with respect to specific modifications, the details thereof are not to be construed as limitations for it will be apparent that various equivalents, changes, and modifications may be resorted to without departing from the spirit and scope thereof, and it is understood that such equivalent embodiments are intended to be included herein.

What is claimed is:

1. A compound represented by the formula

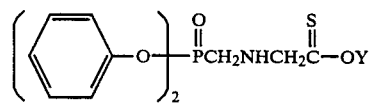

wherein Y is an alkyl group containing 2-6 carbon atoms and the strong acid salts of such compounds.

2. A compound of claim 1 which is ethanethioic acid, 2-[[(diphenoxyphosphinyl)methyl]amino]-O-ethyl ester.

3. A compound of claim 1 which is ethanethioic acid, 2-[[(diphenoxyphosphinyl)methyl]amino]-O-(1-methylethyl) ester.

4. A compound of claim 1 which is ethanethioic acid, 2-[[(diphenoxyphosphinyl)methyl]amino]-O-(2,2-dimethylpropyl) ester.

5. A compound of claim 1 which is a methane sulfonic acid salt.

6. A compound of claim 5 which is ethanethioic acid, 2-[[(diphenoxyphosphinyl)methyl]amino]-O-(2,2-dimethylpropyl) ester methane sulfonic acid salt.

7. A compound of claim 1 which is a p-nitrobenzene sulfonic acid salt.

8. A compound of claim 7 which is ethanethioic acid, 2-[[(diphenoxyphosphinyl)methyl]amino]-O-ethyl ester, p-nitrobenzene sulfonic acid salt.

9. A herbicidal composition comprising an adjuvant and a herbicidally effective amount of a compound represented by the formula

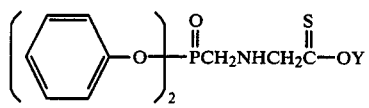

wherein Y is an alkyl group containing 2-6 carbon atoms and the strong acid salts of such compounds.

10. A composition of claim 9 wherein said compound is ethanethioic acid, 2-[[diphenoxyphosphinyl)methyl]amino]-O-ethyl ester.

11. A composition of claim 9 wherein said compound is ethanethioic acid, 2-[[(diphenoxyphosphinyl)methyl]amino]-O-(1-methylethyl) ester.

12. A composition of claim 9 wherein said compound is ethanethioic acid, 2-[[(diphenoxyphosphinyl)methyl]amino]-O-(2,2-dimethylpropyl) ester.

13. A composition of claim 9 wherein said compound is ethanethioic acid, 2-[[(diphenoxyphosphinyl)methyl]amino]-O-(2,2-dimethylpropyl) ester, methane sulfonic acid salt.

14. A composition of claim 9 wherein said compound is ethanethioic acid, 2-[[(diphenoxyphosphinyl)methyl]amino]-O-ethyl ester, p-nitrobenzene-sulfonic acid salt.

15. A method of controlling undesired plants which comprises applying to said plants a herbicidally effective amount of a compound of the formula

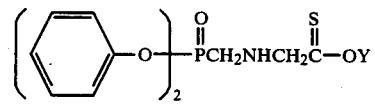

wherein Y is an alkyl group containing 2-6 carbon atoms and the strong acid salts of such compounds.

16. A method of claim 15 wherein said compound is ethanethioic acid, 2-[[(diphenoxyphosphinyl)methyl]amino]-O-ethyl ester.

17. A method of claim 15 wherein said compound is ethanethioic acid, 2-[[(diphenoxyphosphinyl)methyl]amino]-O-(1-methylethyl) ester.

18. A method of claim 15 wherein said compound is ethanethioic acid, 2-[[(diphenoxyphosphinyl)methyl]amino]-O-(2,2-dimethylpropyl) ester.

19. A method of claim 15 wherein said compound is ethanethioic acid, 2-[[(diphenoxyphosphinyl)methyl]amino]-O-(2,2-dimethylpropyl) ester, methane sulfonic acid salt.

20. A method of claim 15 wherein said compound is ethanethioic acid, 2-[[(diphenoxyphosphinyl)methyl]amino]-O-ethyl ester, p-nitrobenzene-sulfonic acid salt.

* * * * *